United States Patent [19]
McKinnon et al.

[11] Patent Number: 5,252,060
[45] Date of Patent: Oct. 12, 1993

[54] INFRARED LASER FAULT DETECTION METHOD FOR HAZARDOUS WASTE INCINERATION

[76] Inventors: J. Thomas McKinnon, 635 Dewey Ave., Boulder, Colo. 80304; J. Houston Miller, P.O. Box 355, Barnesville, Md. 20838

[21] Appl. No.: 859,002

[22] Filed: Mar. 27, 1992

[51] Int. Cl.⁵ .............................................. F23N 5/00
[52] U.S. Cl. ..................................... 431/12; 431/76; 250/338.5; 250/345; 356/437; 356/435
[58] Field of Search ............................ 431/2, 12, 76; 236/15 E; 250/338.5, 345; 356/437, 435

[56] References Cited

U.S. PATENT DOCUMENTS

| | | | |
|---|---|---|---|
| 2,874,763 | 2/1959 | Hobbs | 431/76 |
| 3,701,622 | 10/1972 | Ducasse | 431/76 |
| 3,893,771 | 7/1975 | Bell | 250/345 |
| 4,043,742 | 8/1977 | Egan et al. | 431/12 |
| 4,208,129 | 6/1980 | Spencer | 356/435 |
| 4,426,640 | 1/1984 | Becconsall et al. | 356/437 |
| 4,690,634 | 9/1987 | Herngren et al. | 431/76 |
| 4,849,637 | 7/1989 | Cerff et al. | 250/345 |
| 4,913,647 | 4/1990 | Bonne et al. | 431/76 |
| 5,002,391 | 3/1991 | Wolfrum et al. | 356/437 |
| 5,112,215 | 5/1992 | Frish et al. | 431/76 |

Primary Examiner—Carroll B. Dority
Attorney, Agent, or Firm—Karen Stephan Young

[57] ABSTRACT

An optical method for monitoring the products of combustion, particularly for the detection of upset conditions in the incineration of hazardous waste, is disclosed. On-line detection of upsets is extremely important to avoid sending untreated waste out the stack plume and to avoid the formation of hazardous products of incomplete combustion, such as dioxins. Small hydrocarbons are the strongest candidates for in situ monitoring of combustion efficiency. The combustion is monitored via infrared absorption using tunable diode lasers (TDLs).

18 Claims, 8 Drawing Sheets

INFRARED LASER FAULT DETECTION METHOD FOR HAZARDOUS WASTE INCINERATION

BACKGROUND OF THE INVENTION

1. Field of the Invention

This invention relates to a method for monitoring the products of combustion, particularly in the area of hazardous waste combustion, using optical methods, namely infrared adsorption using tunable diode lasers. It also relates to the field of feedback process control.

2. Prior Art

Hazardous substances are materials which may pose a danger to living organisms, materials, structures, or the environment, by explosion or fire hazards, corrosion, toxicity to organisms, or other detrimental effects. Hazardous waste is a hazardous substance which has been discarded, abandoned, neglected, released, designated as a waste material, or one which may interact with other substances to be hazardous. Some examples of hazardous substances or hazardous waste include, aliphatic and aromatic solvents, chlorinated aliphatics, chlorinated aromatics, nitro-aliphatics, nitro-aromatics, materials containing heavy metals, aqueous-phase materials which contain traces of hazardous components, mixed hazardous wastes (organic solvents with radionuclides), mixtures of materials, and the like. Destruction of hazardous materials has become a major issue in recent years as conventional disposal methods such as land filling and deep well injection become less acceptable. The Resource Conservation and Recovery Act (RCRA) of 1976 makes technologies which mineralize hazardous waste (i.e. convert them to $CO_2$, $H_2O$, HCl, and the like) more attractive. The RCRA statutes require that hazardous wastes in the category of principle organic hazardous components (POHCs) have destruction and removal efficiencies (DREs) of 99.99% or better. If the wastes contain chlorinated dibenzo-p-dioxins, chlorinated dibenzofurans, or chlorinated phenols, the EPA "dioxin rule" requires a DRE of 99.9999%.

There are several available technologies for hazardous waste destruction such as bio-degradation and plasma arc processing, but the most developed destruction method is incineration. A perfectly controlled incinerator can easily meet the mandated DREs because of both the thermodynamic driving force to convert the waste to benign products and the rapid chemical kinetics of oxidation. Real incinerators, however, cannot always be perfectly controlled and a current deficiency in incinerator technology is the lack of a rapid process monitor to detect periods in which combustion is less than ideal. If such a process monitor existed, it could be coupled into a feedback control system which would modify combustion conditions (e.g., decrease fuel flow rate) to bring the emissions back into design limits.

There are several possible causes for cases in which the target DREs are not met. First, the primary combustion zones in an incinerator are highly turbulent. Thus, there exists a non-zero statistical chance that a packet of fuel can pass through this zone without being well mixed with oxygen and oxidizing free radicals. Second, the colder walls of the incinerator can create a quench zone in which material is not fully oxidized. Lastly, there could be equipment failure or operator error which causes large quantities of hazardous waste to pass through the incinerator untreated or made more hazardous.

It is this last condition for which very rapid detection of the upset condition is required. For example, if the incinerator is treating waste covered by the "dioxin rule", then the entire annual "budget" for emissions is used up in 30 seconds. An on-line diagnostic method would also help convince the public that a waste incineration process is operating as designed. The present invention relates to a sensitive, diagnostic method for rapid, on-line monitoring of combustion processes in general and hazardous waste incineration in particular.

The present invention is believed to be an improvement over the present methods of monitoring combustion emissions. Present monitoring methods are limited to monitoring the flue or stack gases of combustion plants. This allows for less control over the combustion process and for a greater chance that hazardous materials will escape before the fault can be corrected. As discussed below, the method of the present invention is designed to monitor combustion emissions in the combustion chamber itself. Additionally, the method of the present invention preferably monitors compounds which are indicators of poor combustion efficiency, another improvement over the present monitoring methods.

SUMMARY OF THE INVENTION

The present invention is directed to a process for monitoring combustion emissions. In particular, the process monitors emission compounds which have strong correlations with poor combustion or low destruction and removal efficiencies. In a preferred embodiment of the present invention, when these compounds which are indicators of poor combustion efficiency are detected, the monitor used to detect these compounds is preferably coupled with a feedback control system which can then modify combustion conditions to bring the emissions back within desired limits, for example, those mandated by statute. As part of the process of the present invention the monitoring device is a laser which is capable of measuring infrared absorption, for example.

The invention broadly encompasses a method for controlling or monitoring the destruction and removal efficiency of a hazardous waste incinerator by monitoring the emitted concentrations of small hydrocarbons. The hydrocarbons include saturated, unsaturated, and substituted hydrocarbons ranging from $C_1$ to $C_4$. The method involves a detection scheme, based on optical devices or extractive sampling and analysis, which monitors the concentrations of the hydrocarbons; a control algorithm, software and/or hardware based, which determines control action based on the hydrocarbon concentrations; and control implementation hardware, such as air flow controllers, fuel flow controllers, and secondary oxidizer input controllers.

Another broad embodiment of the method involves a method for controlling any chemical processing operation, by using infrared absorption of light by gas-phase feedstock, intermediate, or product. The method involves a detection scheme for a gas-phase component or components based on infrared light absorption levels using a tunable diode laser as a light source; a computational section, software and/or hardware based, which computes the concentration or concentrations from the infrared absorption levels; a control algorithm, software and/or hardware based, which determines control action based on the species concentrations; and control implementation hardware which takes the required control actions.

OBJECTS OF THE INVENTION

It is an object of the present invention to supply a long-felt need in the art for a diagnostic method for rapidly monitoring combustion emissions from within the combustion chamber.

It is another object of the present invention to provide a diagnostic method for monitoring the incineration of hazardous wastes.

It is a further object of the present invention to provide a diagnostic method for monitoring combustion emissions which is coupled to a feedback control system which modifies combustion conditions as necessary to bring the emissions back within desired limits.

It is a still further object of the present invention to provide a diagnostic method for monitoring combustion emissions which utilizes a tunable diode laser as its monitoring device.

It is an additional object of the present invention to provide the identity of at least some key intermediates which correlate well with poor destruction and removal efficiency and which are therefore appropriate for monitoring as indicators of combustion problems.

SUMMARY DESCRIPTION OF THE DRAWINGS

Figure 5:
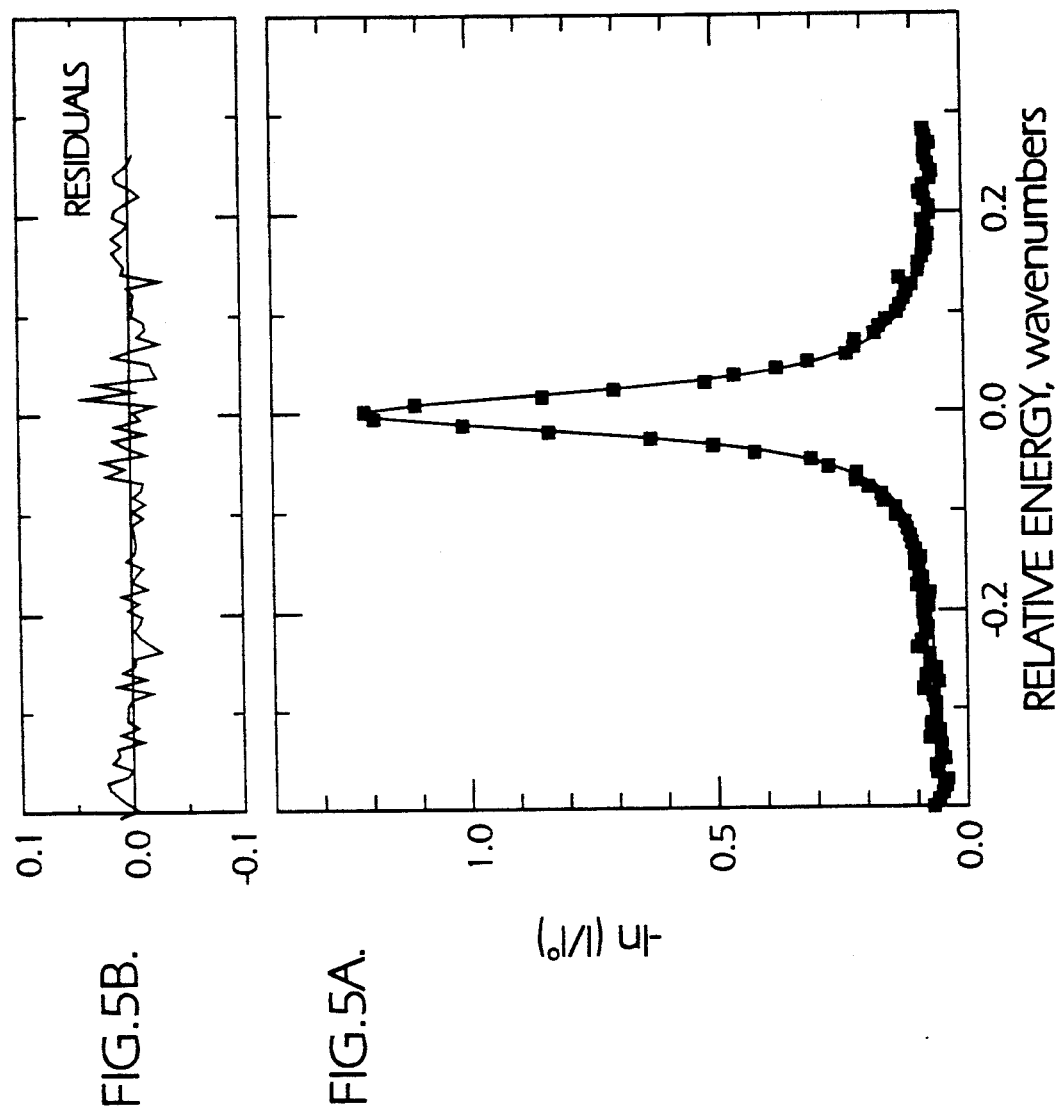

FIG. 5A is a graph showing the fit of the CO P(8) transition in a laminar methane/air diffusion flame assuming a Lorentzian line shape. The spectrus FIG. 5A shows was record at +3.0 mm from the center of the burner and 9 mm above the burner surface. The temperature, was 1157 K.

Figure 6:
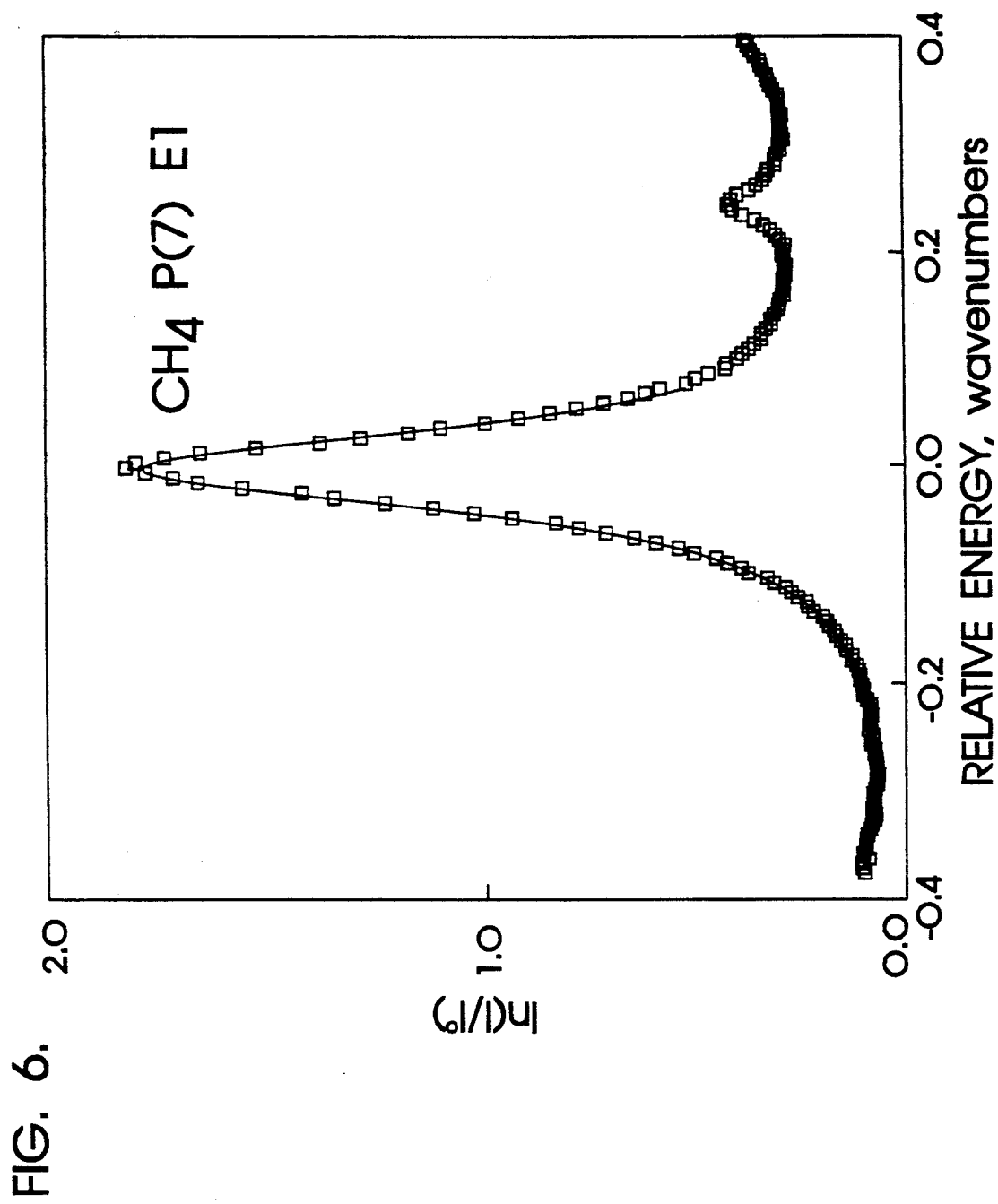

FIG. 6 is a graph showing the fit of the $CH_4$ P(7)E1 of the $\nu 4$ rotational band in a laminar methane/air premixed flame ($\phi = 1.84$) assuming a Lorentzian line shape. The spectrum was recorded 4 mm above the burner surface.

Figure 7B:
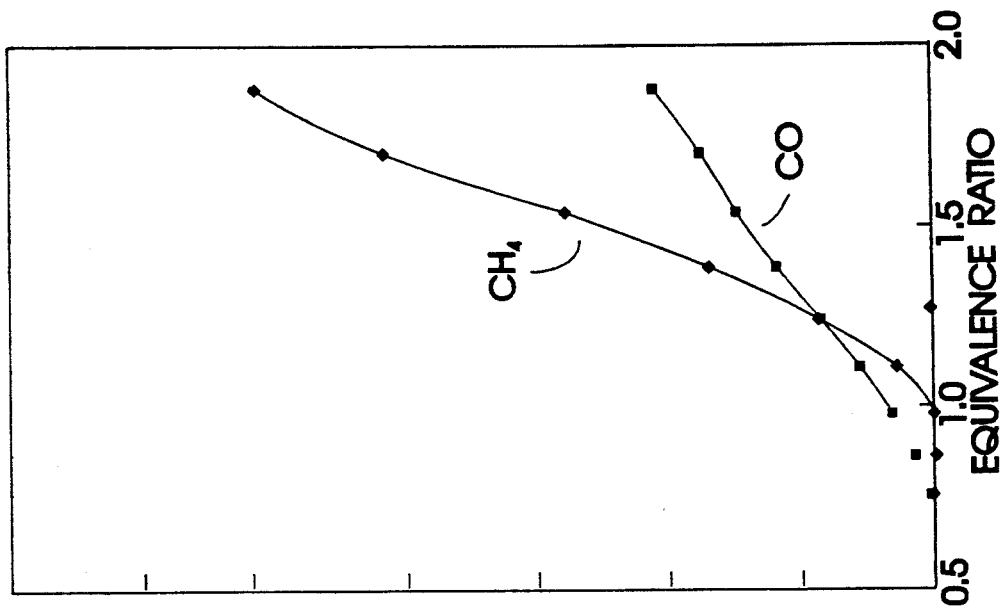
Figure 7A:
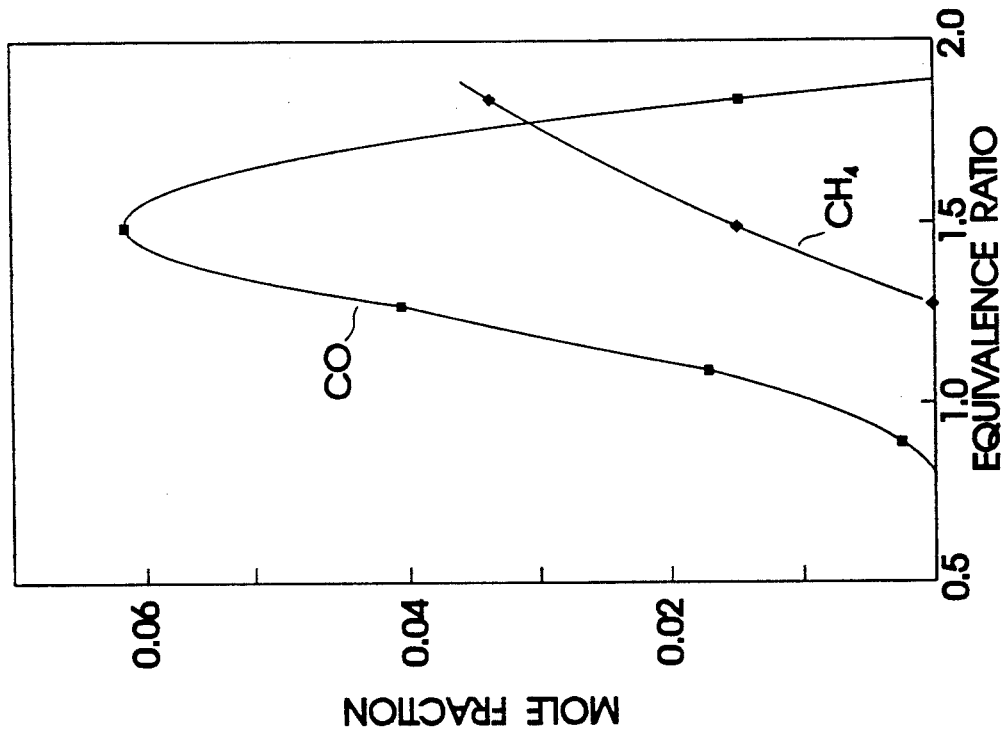

FIGS. 7A and 7B are graphs showing the concentration vs. equivalence ratio for carbon monoxide and methane in the two flame systems studied. For the premixed flame (FIG. 7A) the equivalence ratio is calculated from the overall fuel/air mixture. For the diffusion flame results (FIG. 7B), the local equivalence ratio is calculated from the stoichometry of the local mixture using published quartz microprobe/mass spectrometer results.

Figure 8:
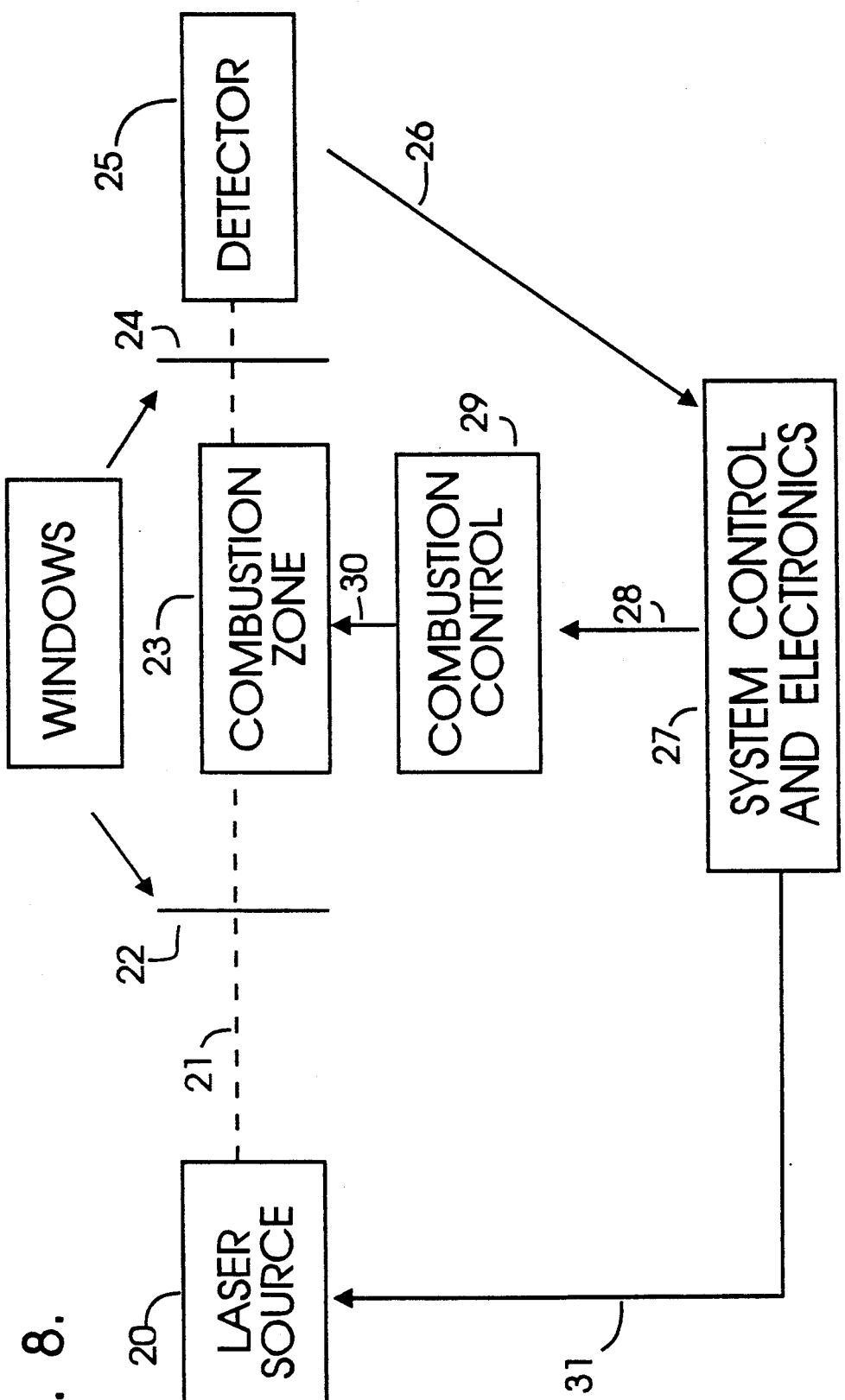

FIG. 8 is a schematic drawing showing the experimental configuration for tunable diode laser diagnostic measurements. In this figure, the laser beam is not split and there is no reference detector.

DETAILED DESCRIPTION OF THE INVENTION AND PREFERRED EMBODIMENTS

In order to effectively monitor combustion emissions, it is preferred that a process monitoring device have a number of properties. First, it preferably monitors continuously or nearly continuously. Second, there is preferably very little lag time from the moment a molecule of waste enters the incinerator until the time its products of combustion are sampled. Third, the device is preferably able to sample a large portion of the combustion chamber or exhaust gases in order to detect spatial inhomogeneities. A property which may or may not be desirable is the ability to detect specific combustion intermediates or transient species. If there exists a strong correlation between process upsets and some global combustion gas property then there is no reason to identify specific gas species. Finally, the device is preferably able to operate in a real industrial environment (i.e., dirty, noisy, vibrations, and the like) and to be operated by personnel without a high degree of technical training.

Extractive sampling methods, such a gas chromatography or mass spectrometry, satisfy some, but by no means all, of the above requirements. For example, the extracted samples can be analyzed for specific species in as much detail as is required. However, they both suffer from a time delay in getting the sample out of the incinerator and into the detector. In addition, if the probe cannot withstand the harsh environment of the combustion chamber, it is placed in the stack gas, which is a less preferable location. Since the gas hold-up times are on the order of seconds in these incinerators, the downstream location of the probe introduces further time delays. The column elution time of gas chromatography adds further delays. These methods would, in general, have a great deal of difficulty in sampling different locations of the gas stream to monitor spatial inhomogeneities. The sampling probe would need to be physically maneuvered about the exhaust stack or multiple sampling probes would be required. A further limitation of extractive sampling is that chemistry continues to occur after the sample is extracted. For example, the hot combustion gases contain a relatively large concentration of free radicals which would react with little or no activation energy in the sampling probe.

Laser-based diagnostic methods, such as those of the present invention, can be nearly ideal methods for identifying incinerator upsets. First, they can be continuous and instantaneous. Pulsed laser sources are not quite continuous, but the typical pulse-to-pulse time is on the order of 100 ms or less. Laser methods can sample any portion of the combustion zone since there is no requirement for a physical probe to withstand the severe oxidative conditions. Optical methods have several ways of sampling large volumes. If the method has a small probe volume, such as laser-induced-fluorescence, then the laser beam and detection optics can be rastered through the combustor volume. If the detection method is based on absorption, then the light beam can follow a folded path several times through the volume. Depending on the method selected, optical diagnostics may have the opportunity to identify selected molecules or radical species. A possible disadvantage of optical methods is in hardening of the equipment to withstand the conditions in a real incinerator. The laser itself is preferably rugged and amenable to handling by technicians without laser experience. Provision is preferably made for keeping optics and windows clean and aligned. The method is also preferably able to operate in the presence of soot, ash, and other particles in the combustion gases.

As stated above, upsets in combustion efficiency can be caused by problems with temperature or due to locally-rich mixtures (poor mixing, equipment failure, operator error). In order to exploit an optical diagnostic method in a incinerator environment, it is preferable to first identify a chemical species or class of species which have two properties. First, the concentration of the key intermediate or intermediates preferably correlates well with poor combustion. That is, they preferably increase or decrease in concentration strongly as the degree of substrate mineralization decreases. Second, they preferably have some convenient optical transition which can be exploited by spectroscopic methods and not be masked by the other species in the combusting mixture. In the examples that follow, test results, which demonstrate the discovery of certain key intermediates which may be useful in monitoring the incineration of hazardous wastes, are summarized. These key intermediates are hydrocarbons as disclosed in Table 1, Example 1, below.

The hydrocarbon chemical species of Table 1 lend themselves to a number of potential visible and ultraviolet optical diagnostic methods, such as resonance-enhanced multiphoton ionization (REMPI), multiphoton laser induced fluorescence (MPLIF), and Raman spectroscopy. Unfortunately, there are significant problems in applying each of these techniques in an environment such as a hazardous waste incinerator. All of these methods suffer from attenuation of the incident light beam by particle scattering. Each is susceptible to interference from non-resonance effects: ionization by other molecular species or particles, or fluorescence from polynuclear aromatic hydrocarbons. Small hydrocarbons such as methane and acetylene have their lowest energy electronic transitions deep in the ultraviolet where these problems are exacerbated. Alternatively, they may be accessible with multiphoton techniques at longer wavelengths but the high laser fluences then required may lead to interference from photolytic effects. Further, REMPI requires the introduction of an electrode for the collection of ions, and thus has equivalent disadvantages as other probe techniques.

An optical method that does not suffer these problems is infrared absorption, specifically using tunable diode lasers. The advantages of using infrared absorption are several-fold. First, monitoring a large volume of the combustion chamber can be done without moving the beam since the absorption is a line-of-sight method. Second, because scattering intensity is proportional to the $\lambda^{-4}$, infrared light may be affected less by soot and small ash particles than visible and UV methods. Third, the tunable diode lasers are solid-state devices and could be made rugged. In addition to making quantitative concentration measurements, the temperature can be measured simultaneously as a redundant check on incinerator performance. The temperature may be a line-of-sight average, but by appropriate selection of lines for study, it can be weighted for the cooler zones.

Both near-infrared and mid-infrared diodes might find use as combustion diagnostics. The former have greater power than the latter, operate at or near room temperature (compared to the cryoscopic source temperatures required for the mid-infrared devices), and are significantly cheaper to purchase and operate. However, line strengths for the vibrational overtones excited by near-infrared lasers are much smaller than the fundamentals in the mid infrared, and light scattering by particles is more severe. Therefore, in the preferred embodiment of this invention, mid-infrared TDLs are preferred.

To demonstrate the application of tunable diode lasers to the detection of hydrocarbon species in combustion systems, preliminary measurements have been made of the concentrations of both carbon monoxide and methane in both a laminar methane/air diffusion flame, supported on a Wolfhard-Parker slot burner, and in a premixed methane/air flame supported on a water-cooled, porous-plug burner. These two systems provide ideal circumstances for the application of TDL diagnostics. They each have a long, homogeneous (in temperature and composition) optical path and each system has been extensively studied, so that the accuracy of the TDL results can be verified.

Figure 1:
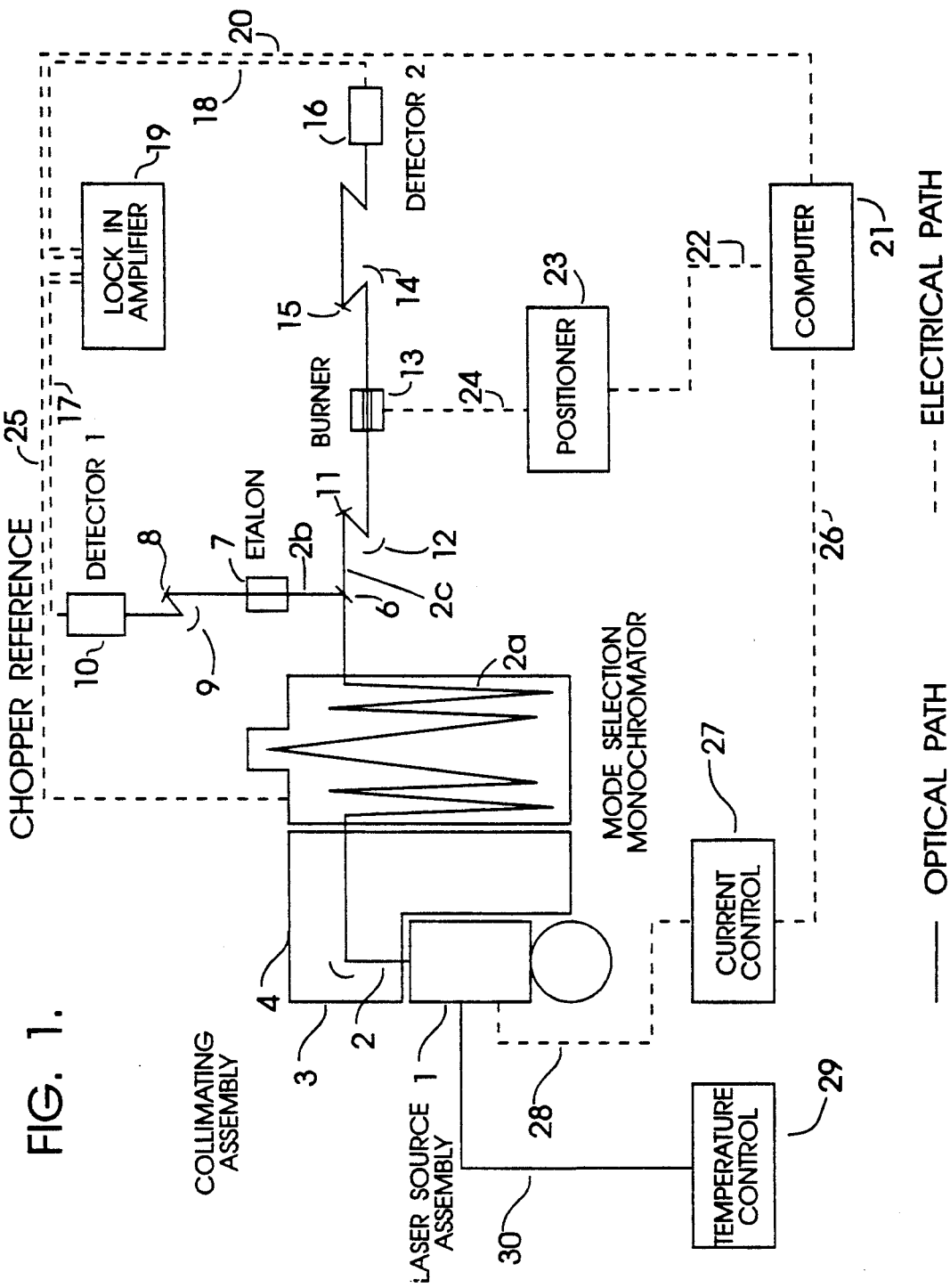
FIG. 1 is a schematic drawing showing the configuration for a tunable diode laser capable of taking diagnostic measurements in laboratory flames.

The laser system and associated optics were identical for each flame studied and have been described in detail previously (Miller, J.H., Elreedy, S., Woldu, F., Ahvaze, B., and Hassanzadeh, P. (1991). Tunable diode laser detection of carbon monoxide in a laminar methane/air diffusion flame: concentration and temperature measurements. *Appl. Optics*, submitted for publication.) and are shown in FIG. 1. This article is incorporated herein by reference.

Mid-infrared tunable diode lasers are miniature semiconductor chips composed of a single crystalline lead salt alloy mounted in a gold-plated copper package. Like all semiconductors, they will conduct electricity when a sufficient voltage is applied. However, these diodes also emit monochromatic, infrared light whose frequency depends on the temperature of the device. With operating temperatures of between $\approx 12$ and $\approx 60$ K, the devices are capable of spectral output over a range of 50–80 cm$^{-1}$. Different stoichiometries used in the synthesis of the diodes can be used to produce spectral windows in the range of 3500 to 350 wave number (wavelengths of 2.8 to 30 $\mu$m).

In the work described in Example 2 below, a diode with spectral output between 2090 and 2160 cm$^{-1}$ used for carbon monoxide. The diode was mounted in a closed-cycle helium refrigerator which is controlled by a cryogenic temperature stabilizer. By adjusting the current through the diodes, slight modifications of temperature caused by Joule heating result in changing spectral output. Similarly, for methane measurements a diode with spectral output between 1250 and 1300 cm$^{-1}$ was used.

Light emitted from the lasers is not collimated and may not be single-mode. In Example 2, the beam was collimated with a parabolic mirror, a Helium-Neon alignment laser beam was superimposed, and the combined beam was then steered around the optical-mounting table using reflective optics and eventually was directed into a liquid nitrogen-cooled InSb detector. The beam could be either electronically modulated or mechanically chopped. In either case the amplified detector signal was processed through a phase sensitive, lock-in amplifier. Digitized output from the lock-in was recorded on an IBM-PC data acquisition system. The overall experimental configuration is shown in FIG. 1. For the methane measurements a HgCdTe detector was used to detect the infrared light.

As shown in FIG. 1, light, indicated by solid line 2, which represents the optical path, is emitted from laser source assembly 1 and passes into collimating assembly 3. In collimating assembly 3 the beam is collimated with a parabolic mirror 4 and a Helium-Neon alignment laser beam is superimposed. The combined light 2a then passes into mode selection monochromator 5 where it is mechanically chopped. The light 2a leaves mode selection monochromator 5 and is split at mirror 6. One beam of light 2b travels through etalon 7. The beam is steered using mirror 8 and parabolic mirror 9 until it reaches detector 1, 10. The other beam of light 2c is steered using mirror 11 and parabolic mirror 12 until it passes through the flame emitted by burner 13. The beam is then steered using parabolic mirror 14 and mirror 15 until it reaches detector 2, 16. Electronic signal 17 from detector 1, 10 and electronic signal 18 from detector 2, 16 are sent to lock-in amplifier 19. Digitized output 20 from lock-in amplifier 19 is sent to and recorded on computer 21. Electronic signal 22 travels from computer 21 to positioner 23. Electronic signal 24 from positioner 23 travels to burner 13. Chopper reference signal 25 from lock-in amplifier 19 travels to mode selection monochromator 5. Electronic signal 26 travels from computer 21 to current control 27. Electronic signal 28 travels from current control 27 to laser source assembly 1. Electronic signal 30 travels from temperature control 29 to laser source assembly 1.

Figure 2:
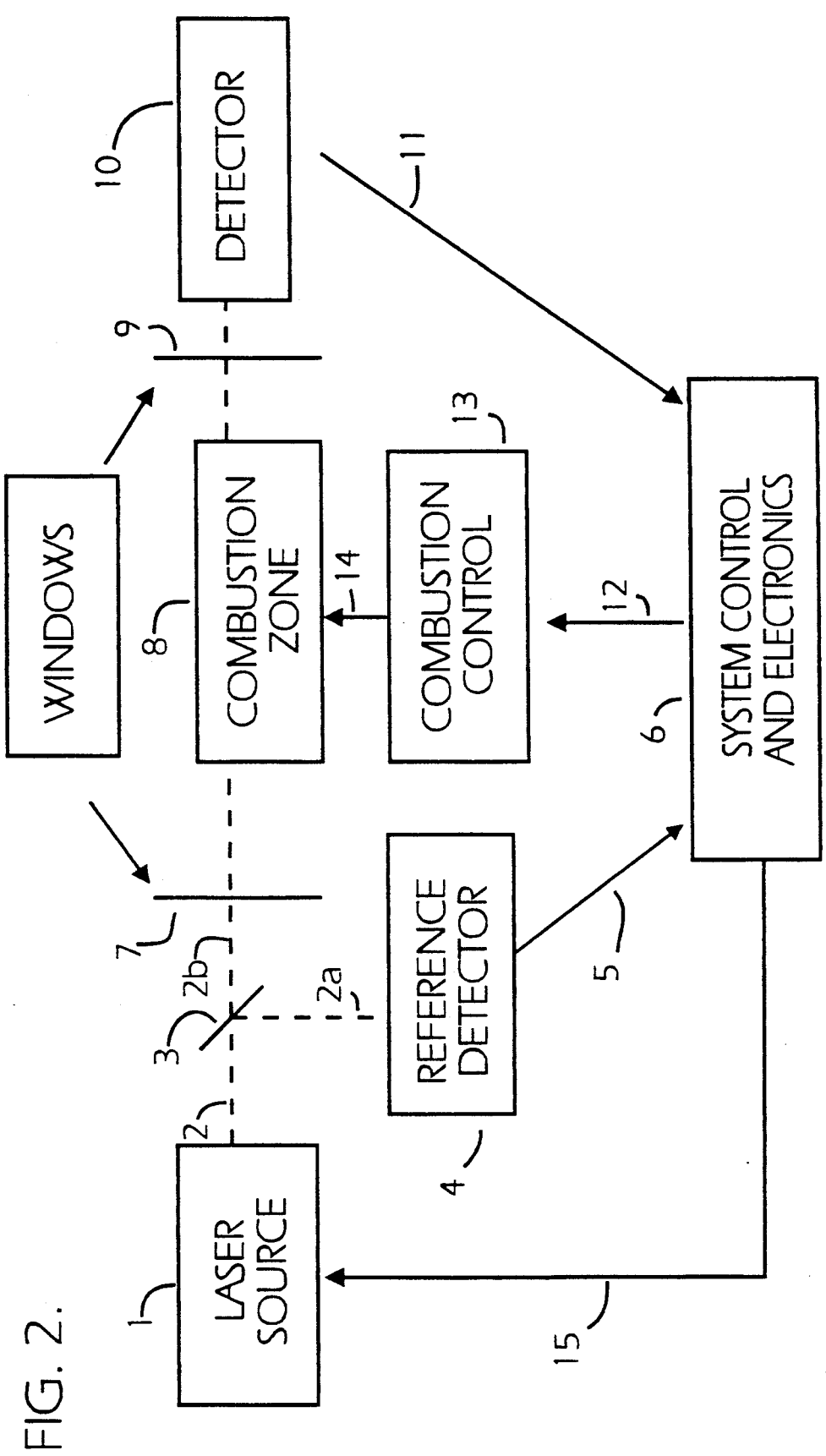
FIG. 2 is a schematic drawing showing the experimental configuration for tunable diode laser diagnostic measurements. In this figure, the laser beam is split, with one of the beams being detected by a reference detector and the other being detected by a sample detector.

FIG. 2 illustrates schematically the preferred embodiment of the present invention and presents the method of using a tunable diode laser to monitor a combustion process. Laser beam 2 exits from laser source 1. Laser source 1 includes a collimating assembly and laser beam 2 is preferably collimated prior to exiting from laser source 1. Laser beam 2 is optically split using optical splitter 3. A portion of the beam 2a is directed into a reference detector 4. The remaining beam 2b is directed through window 7 into combustion zone 8 and continues through window 9 to detector 10. Windows 7 and 9 are made of any infrared transparent substance known to the art and are located on opposite sides of combustion zone 8. Prior to leaving laser source 1, beam 2 is preferably mechanically chopped and/or electronically modulated by means known to the art. Electronic signal 5 from reference detector 4 travels to system control and electronics unit 6. Electronic signal 11 from detector 10 travels to system control and electronics unit 6. Electronic signal 12 travels from system control and electronics unit 6 to combustion control unit 13. Electronic signal 14 travels from combustion control unit 13 to combustion zone 8. Electronic signal 15 travels from system control and electronics unit 6 to laser source 1.

In the preferred embodiment of the present invention, the laser beam is both mechanically chopped and electronically modulated.

The reference detector shown in FIG. 2 may, for example, be a low pressure reference transmission cell containing a sample of the gas under study. In this embodiment, the signal from the reference detector could be used to provide laser frequency stabilization through a feedback circuit via the system control and electronics unit. Alternatively, in another embodiment, the reference detector could contain an etalon and the output could be used for relative frequency calibration. Alternatively, in still another embodiment, the reference detector could consist of only the infrared detector alone and the output could be used to provide a reference intensity.

FIG. 8 illustrates schematically another embodiment of the present invention and presents another method of using a tunable diode laser to monitor a combustion process. Laser beam 21 exits from laser source 20. Laser source 20 includes a collimating assembly and laser beam 21 is preferably collimated prior to exiting from laser source 20. Laser beam 21 is directed through window 22 into combustion zone 23 and continues through window 24 to detector 25. Windows 22 and 24 are made of any infrared transparent substance known to the art and are located on opposite sides of combustion zone 23. Prior to leaving laser source 20, beam 21 is preferably mechanically chopped and/or electronically modulated by means known to the art. Electronic signal 26 from detector 25 travels to system control and electronics unit 27. Electronic signal 28 travels from system control and electronics unit 27 to combustion control unit 29. Electronic signal 30 travels from combustion control unit 29 to combustion zone 23. Electronic signal 31 travels from system control and electronics unit 27 to laser source 20.

Since there is no reference detector in this embodiment of the present invention, the operator preferably scans wavelengths in order to obtain results. A measurement is made at a wavelength which is in the middle of the absorption feature for the substance being scanned. A second measurement is then made at a wavelength which is representative of non-absorption. The two results are then compared.

In both the embodiments shown of the present invention, the laser beam is both mechanically chopped and electronically modulated.

The system control and electronics unit shown in FIGS. 2 and 8 may, for example, consist of one or more lock-in amplifiers to provide phase-sensitive detection of both reference and sample signals. In an embodiment of the present invention, the sample detector signal could be split into two portions. One of these signals could be fed into a lock-in amplifier whose reference would be the reference mechanical chopping frequency. The resulting lock-in amplifier output would provide a reference intensity ($I^o$). The second signal could be fed into another lock-in amplifier whose reference frequency was twice the injection current modulation frequency.

It is envisioned that the system and electronics control unit would provide feedback information into a combustion control unit. This could allow the for rapid changes and corrections of any faults in the combustion zone. For example, the feedback information can be fed to an air input controller or a fuel input controller for the combustion chamber. Additionally, the feedback information can be fed to a secondary oxidizer input controller for the combustion chamber. The secondary oxidizer can be pure oxygen, ozone, or any other gaseous oxidizing compound. By monitoring emissions from the combustion process, and using the feedback information, the various controllers for the combustion chamber can effectively maintain the destruction and removal efficiency of the combustion chamber.

It has been demonstrated that the sensitivity of TDL measurements can be increased by modulating the laser wavelength. If the modulation frequency is large with respect to the feature width (also expressed in frequency), then the technique is known as frequency modulation spectroscopy. The inverse case (relatively low modulation frequencies) is known as wavelength modulation or derivative spectroscopy. Wavelength modulation spectroscopy is touted to improve sensitivities 3 orders of magnitude over conventional absorption detection. Frequency modulation extends sensitivities even further, perhaps another 3 orders of magnitude. It is contemplated that both wavelength modulation and frequency modulation will be performed on the laser beam using the method of the present invention. The resulting increased sensitivity allows for tight monitoring of even slight changes in the combustion zone and, through the feedback to the combustion control unit, for rapid changes in the combustion zone to correct any problems.

As the technology exists today, cryogenic cooling of both sources and detectors is required. Recent advances have pushed upward the source temperatures such that many diodes are available today which require only liquid nitrogen cooling rather than the more elaborate closed cycle helium refrigerators. Future improvements in manufacturing may move source cooling requirements to temperatures attainable with thermoelectric coolers.

Because of the sometimes complicated mode structure of these devices, significant operator control is required. Further manufacturing advances may help alleviate this concern. Alternatively, it is possible that an expert control system could be designed to minimize the requirements for human operator control. The research systems currently available are by their nature quite delicate. Hardening for industrial use is preferably required. In a noisy industrial environment significant signal averaging may be required to achieve satisfactory signal to noise ratios (SNRs). Both sweep integration techniques and modulation techniques have been applied to TDL measurements to dramatically increase sensitivity: with modulation frequencies of 100 kHz, concentration measurements in the sub-ppm range are attainable in a few seconds of data acquisition time. This would be fast enough to serve as a system fault indicator and much faster than that required for permit certification. In the method of the present invention, modulation techniques preferably provide overall greater sensitivity than sweep integration techniques.

While this invention is well suited to monitoring the incineration of hazardous waste, it is not limited to monitoring hazardous waste combustion. The process of feedback control based on absorption levels of infrared light from a TDL can be applied to the control of any process which has gas-phase reagents (feedstocks), intermediates, or products which can be detected by TDLs, namely those having absorption levels in the mid-infrared or near-infrared.

The present invention details an analysis of optical methods for the detection of upset conditions in the incineration of hazardous waste. On-line detection of upsets is extremely important to avoid sending untreated waste out the stack plume or the formation of hazardous PICs (e.g., dioxins). The analysis was conducted by running numerical simulations of hazardous waste combustion using detailed elementary chemical kinetic mechanisms. The results of the simulations were examined to select the components which had strong correlations with poor combustion. It was found that small hydrocarbons are the strongest candidates for in situ monitoring of combustion efficiency.

The optical method which comes closest to meeting the requirements for an ideal process monitor is infrared absorption using tunable diode lasers. These devices provide sensitive, species-specific detection capability for many of the target hydrocarbons.

The disclosure of the present invention is further enhanced by the Examples which follow. A description of the tests included in the Examples can be found in McKinnon, J.T., Miller, J.H., and Abraham, E. (1992). An infrared laser fault detection method for hazardous waste incineration. *Combust. Sci. and Tech.*, submitted for publication. This article is incorporated herein by reference.

EXAMPLE 1—KINETIC MODELING

In searching for key intermediates which correlate well with poor combustion, in particular in the case of ineffective incineration of hazardous wastes, chemical kinetic modeling of the oxidation of two chlorinated materials was conducted. Numerical chemical kinetic models of chlorinated hydrocarbon (CHC) oxidation at several different temperatures and equivalence ratios were conducted and the computed product spectra were examined. From these models it was possible to identify the specific compounds which correlate strongly with poor destruction.

Chlorine is known to have a number of effects on flame chemistry. The weak C—Cl bond leads to accelerated thermal fuel decomposition and increased rates of soot formation on the fuel side of a diffusion flame. Chlorine atom also competes for H-atom which reduces combustion rates and flame velocities.

The combustion was modeled as a perfectly stirred reactor (PSR) with a 50-ms residence time. A PSR has infinite backmixing; that is, a packet of entering fuel/air is immediately dispersed throughout the combustor volume. The PSR model roughly describes the fluid mechanics of the highly turbulent primary combustion zone of a typical hazardous waste incinerator. The Chemkin chemical kinetics package of Sandia National Laboratories was used for the simulations.

The elementary reaction mechanism for chlorinated species was developed by Miller (Miller, G.P. (1989). Modeling flat flames burning chlorinated methanes in a methane/air environment. Ph.D. thesis. Louisiana State University.). This mechanism contains 340 elementary reactions and includes both chlorinated and non-chlorinated hydrocarbons of one and two carbons, oxygenated species, and free radicals.

The combustion of both methyl chloride and trichloroethylene (TCE) were modeled. Methyl chloride was chosen as a model compound to represent chlorinated alkyl molecules while TCE was chosen because it is used in large quantities as an industrial solvent. The methyl chloride was oxidized directly with air while the TCE was diluted with methane to produce a hydrogen-to-chlorine ratio of 2:1. Incinerators maintain the H/Cl ratio well above unity to avoid the formation of molecular chlorine, which is much more difficult than HCl to scrub from the stack gas.

The model was run at equivalence ratios from 0.8 to 2.0 and at temperatures of 923° C., 1223° C., and 1523° C. In all, 42 different numerical simulations were run. The following criteria were adopted for selection of a combustion intermediate to use as an indicator of poor combustion. First, compounds having strong sensitivity to equivalence ratio, $$\frac{X_{\phi=2.0}}{X_{\phi=1.0}} \geq 10 \quad (1)$$

where X is the species mole fraction and $\phi$ is the equivalence ratio, were chosen. The second criterion was that the concentration had to be greater than 1 ppm to allow for detection by optical methods. These criterion were somewhat loosely applied. For example, if the concentration ratio was much greater than 10, but the absolute concentration was slightly below 1 ppm, the species was still included in the list.

Table 1 shows the results of these decision criteria applied to the model simulations. The vertical order in this table is in order of the concentration ratio at $\phi=2.0$ over $\phi=1.0$ (as in Equation 1).

TABLE 1

Intermediates of combustion in a perfectly-stirred reactor numerical simulation which have (1) a strong correlation with equivalence ratio and (2) a concentration greater than 1 ppm.

| 923° C. | | 1223° C. | | 1523° C. | |
|---|---|---|---|---|---|
| TCE/CH$_3$Cl | CH$_4$ | CH$_3$Cl | TCE/CH$_4$ | CH$_3$Cl | TCE/CH$_4$ |
| No PICs meet criterion | | C$_2$H$_6$ | C$_2$H$_2$ | C$_2$H$_4$ | C$_2$H$_2$ |
| | | CH$_4$ | C$_2$H$_6$ | C$_2$H$_2$ | C$_2$H$_4$ |
| | | CH$_3$OH | C$_2$H$_4$ | CH$_3$OH | C$_2$H$_2$O |
| | | C$_2$H$_4$ | CH$_4$ | CH$_4$ | CH$_4$ |
| | | CH$_3$Cl | C$_2$Cl$_2$ | CH$_3$ | CH$_3$Cl |
| | | CH$_2$O | | C$_2$H$_2$O | CH$_3$ |
| | | CH$_2$O | | C$_2$HCl | C$_2$HCl |
| | | H$_2$ | | CH$_3$Cl | C$_2$Cl |
| | | H$_2$O$_2$ | | CH$_2$O | C$_2$Cl$_2$ |

At 923° C., none of the intermediates of combustion met the criterion of Eq. 1. This temperature is so low, however, that it represents a gross failure mode in the model. An on-line optical diagnostic method would pick up this failure before the temperature got so low. At the two higher temperatures, there were a number of molecules and free radicals which met the criteria. An extremely interesting feature of this table is that only a very few chlorinated species were present.

Although the absence of chlorinated species may have not been expected, it is perfectly reasonable in light of the relative weakness of the C—Cl bond. The alkyl C—Cl bond has a bond dissociation energy (BDE) in the range of 80 to 85 kcal/mol which is about 15 to 20 kcal/mol weaker than an equivalent C-H bond. Thus the chlorine-carbon bond of the parent molecule has a strong tendency to thermolytically cleave as the feed enters the incinerator and this type of bond has little tendency to reform in the high temperature combustion zone. This is not to say that chlorinated molecules are not formed by improperly operated incinerators. In the cooler stack gases, the free C$_1$ atoms rapidly add to unsaturated species and displace hydrogen, forming potentially dangerous compounds such as vinyl chloride.

Based on the elementary reaction mechanism as shown in Table 1, it was unanticipatedly concluded that the best on line diagnostic method to use to avoid production of hazardous chlorinated products of incomplete combustion (PICs) is not to monitor the PICs themselves, but to monitor their hydrocarbon precursors in the combustion zone. If the hydrocarbon concentrations are kept low, then the CHC compounds cannot form in the cooler stack gas because there are no carbon backbones on which to build. While hydrocarbons were found in this model to be the best subjects for monitoring, the method of the present invention is not limited to monitoring small hydrocarbons. Any emission intermediates showing a strong correlation to destruction and removal efficiency can be monitored. These materials may be free radicals, chlorine-containing molecules, and oxygen-containing molecules, for example. If they meet the criteria of Equation 1 above and have concentrations of at least 1 ppm, they are candidates for monitoring.

Figure 3:
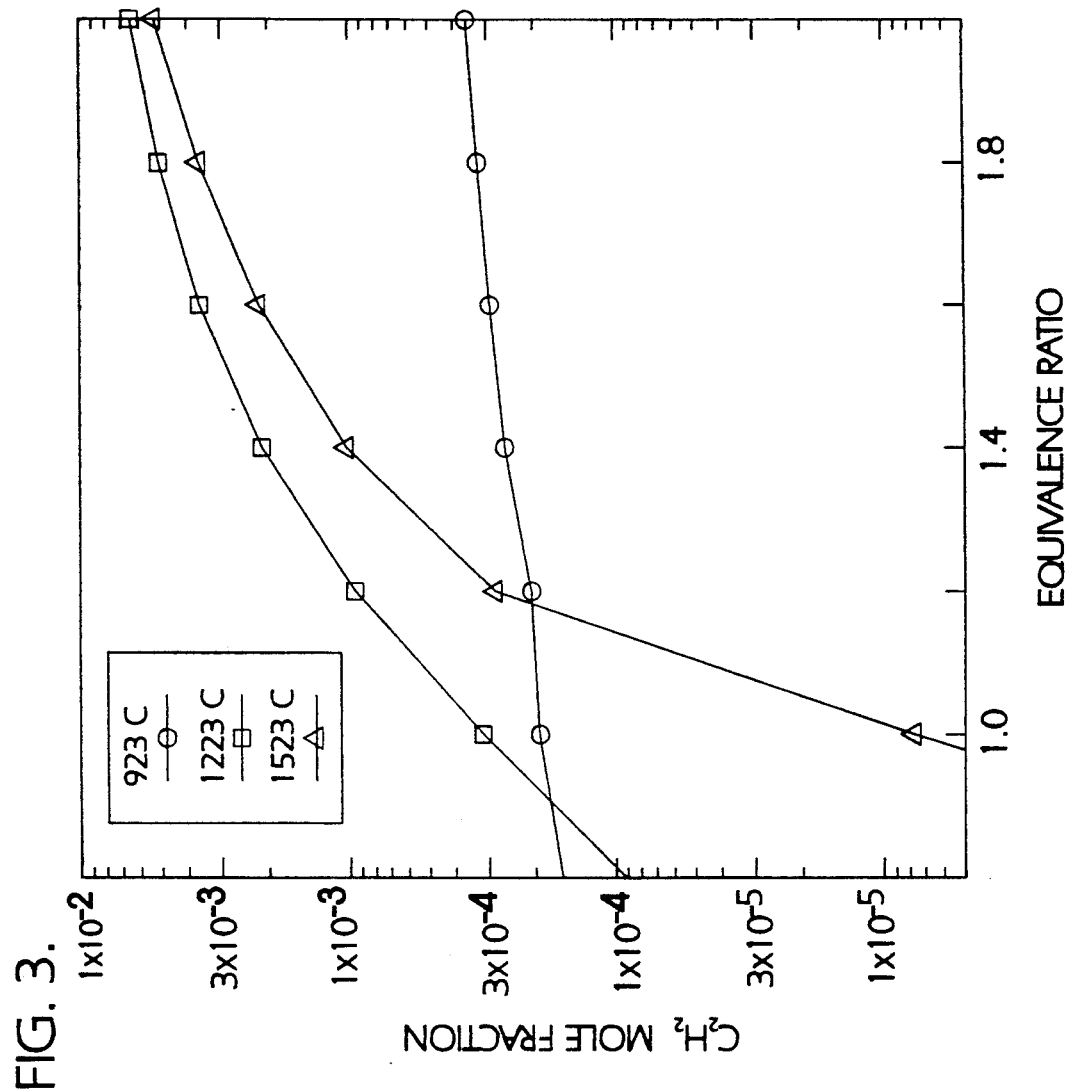
FIG. 3 is a graph showing a model prediction of acetylene concentration in a perfectly stirred reactor burning methylene chloride/air as a function of equivalence ratio.
Figure 4:
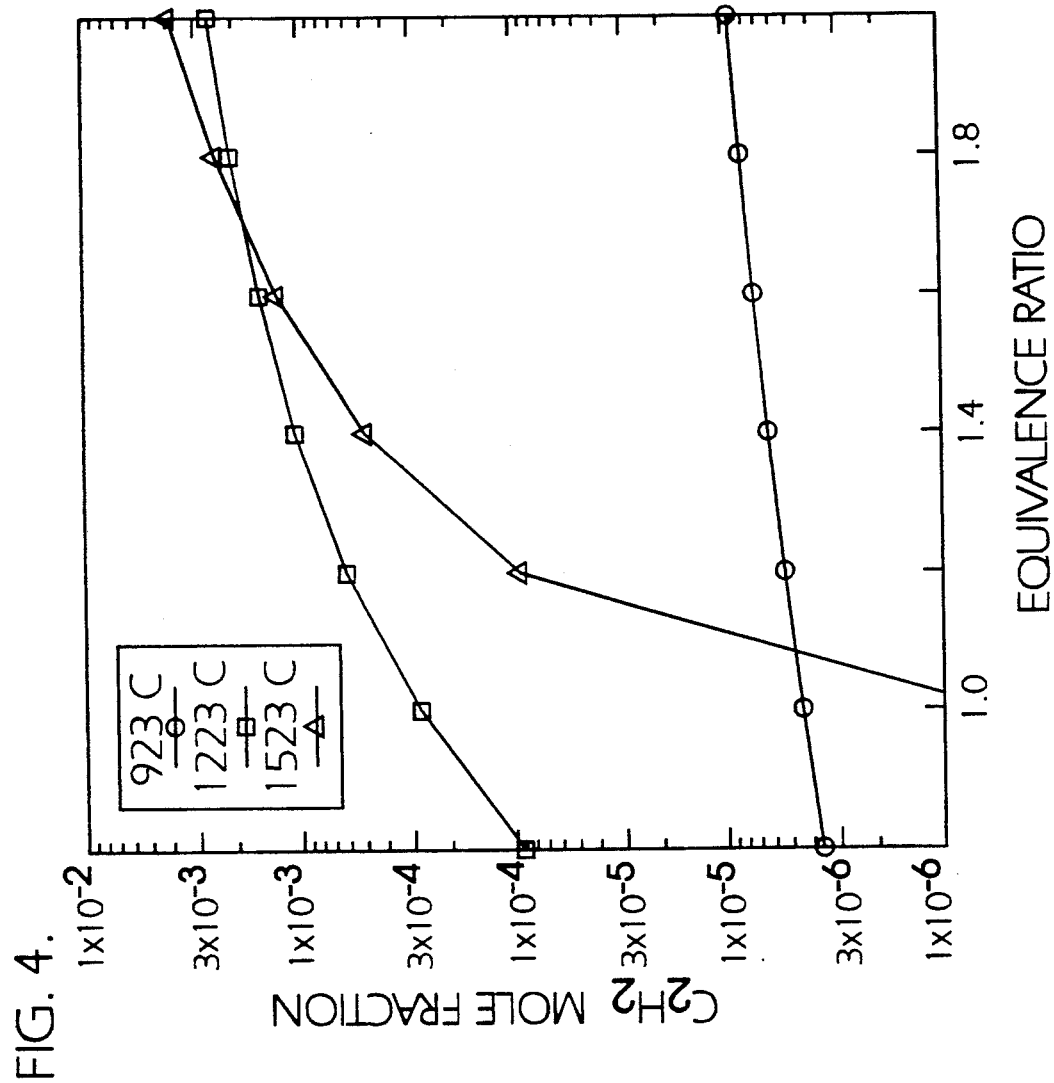
FIG. 4 is a graph showing a model prediction of acetylene concentration in a perfectly stirred reactor burning a mixture of trichloroethylene (TCE)/methane in air as a function of equivalence ratio. The TCE/methane ratio is set for a H:Cl ratio of 2.0.

FIGS. 3 and 4 show the behavior of one of the species from Table 1, acetylene, in a PSR as a function of equivalence ratio, as predicted by the model. FIG. 3 shows the model results for methyl chloride combustion and FIG. 4 shows the results for TCE/methane combustion. At the highest temperature, 1523° C., which is representative of the temperature of the primary combustion zone of an incinerator, the sensitivity of C$_2$H$_2$ concentration to equivalence ratio is extremely steep; a 20% change in $\phi$ results in a 20-fold change in concentration. In the case of methyl chloride, acetylene concentration is a very good indicator of temperature as well, which can be seen by comparing [C$_2$H$_2$] at $\phi=1.0$ for the three different temperatures. The simulations of TCE/CH$_4$ show that the [C$_2$H$_2$] rises at 1223° C. but falls again at 923° C. As stated above, the 923° C. condition represents such a gross failure mode, that an optical on-line monitoring device would have sounded a warning long before the temperature fell this low.

EXAMPLE 2—TDL DETECTION OF HYDROCARBON SPECIES IN COMBUSTION ENVIRONMENTS

The laser system was a commercial configuration manufactured by Laser Photonics/Analytics Division. The set-up appeared as shown in FIG. 1. Diodes, mounted in a closed-cycle helium refrigerator, were operated between 2090 and 2160 cm$^{-1}$ (for CO) or 1250 and 1280 cm$^{-1}$ (for CH$_4$). The output from the laser was collimated, the beam from a helium-neon alignment laser was superimposed, and the combined beam which emerges with a diameter of $\approx 8$ mm, was passed through a mode-selection monochromator typically operated with a 1.0-1.5 cm$^{-1}$ bandwidth. The beam was steered around the optical mounting table using reflective optics and was eventually directed into either a HgCdTe (for $\lambda > 5$ $\mu$m, $\nu > 2000$ cm$^{-1}$) or a InSb (for $\lambda > 5$ $\mu$m, $\nu < 2000$ cm$^{-1}$) detector. The beam was focussed into the flame and recollimated using a pair of 500 mm f.l. spherical mirrors. The full-width-at-half-maximum of the resulting beam was 400 $\mu$m.

The diffusion flame studied was identical to that which has been used for the last six years and which has been extensively characterized. The methane/air premixed flame was supported on a water-cooled McKenna porous-plug burner with an argon shroud. Fuel was metered through a rotameter. Air flow was monitored with a Hastings mass flow meter. Both flow measuring devices were calibrated against a bubble flow meter. The specific flow rates were chosen to keep the total volumetric flow rate through the burner nearly constant at 8 Lpm. Five different equivalence ratio flames were studied from $\phi=0.85$ to $\phi=1.95$. Spectra were recorded at two heights in the flame: 4 mm and 12 mm above the burner surface. For isolated lines, the lineshape fitting programs require a temperature to be input. Temperatures were measured with a 0.005" Pt/Pt-Rh thermocouple with a bead diameter estimated to be approximately 300 μm. Radiation losses from the thermocouple were estimated assuming a spherical geometry.

In both flame systems the extinction of the infrared laser beam through the flame for spectral scans across a number of individual rotational lines for carbon monoxide and methane was monitored. Absorption of infrared light by a molecule in the laser beam is described by the Bouger-Lambert law which, for a uniform line-of-sight measurement, can be expressed as:

$$T_\nu = \left(\frac{I}{I^\circ}\right) = \exp(-S \cdot g(\nu - \nu^\circ) \cdot P_j \cdot L) \qquad (2)$$

In this equation, $T_\nu$ is the transmissivity at frequency $\nu$; $I^\circ$ and $I$ are the beam intensities before and after the absorbing sample, respectively; S is the line strength for the absorption transition; $g(\nu-\nu^\circ)$ is the line shape factor (typically described assuming either a Voigt or a Lorentzian profile for the wavelength dependence of the absorption); $P_j$ is the partial pressure of the absorbing species; and L is the path length. For carbon monoxide, the line strength is the overall transition band strength multiplied by the fractional population of the absorbing rotational level given by:

$$f = (2J+1) \cdot \left(\frac{hB}{kT}\right) \cdot \exp\left(-\frac{\nu h \omega_e}{kT}\right) \cdot \left(1 - \exp\left(-\frac{h\omega_e}{kT}\right)\right) \qquad (3)$$

where J is the rotational quantum number and v is the vibrational quantum number for the absorbing state, B is the molecule's rotational constant, and $\omega_e$ is the frequency of the absorption in the absence of rotational excitation. The situation is somewhat more complicated for methane. However, accurate measurements of individual methane absorption line strengths have been made at room temperature, which can be extrapolated to flame temperatures.

FIG. 5B shows an absorption across the P(8) rotational level of carbon monoxide in the methane air diffusion flame at a height of 9 mm above the burner surface and +3 mm from the plan symmetry running through the center of the burner. FIG. 5A shows a three parameter fit of the data with the independent parameters being the partial pressure (mole fraction) of carbon monoxide, the baseline level, and the room temperature collision halfwidth. The baseline level keeps track of non-resonant effects which might include extinction due to particles and beam-steering in the flame's steep temperature gradients. The halfwidth at flame temperatures is calculated from the room temperature value assuming a $T^{-0.67}$ dependence. Band strength measurements reported by Hanson et al. (1980), Absorption spectroscopy of combustion gases using a tunable IR diode laser. In *Laser Probes for Combustion Chemistry*, D.R. Crosley, ed., ACS Symposium Series No. 134, American Chemical Society, Washington, D.C., were used in the fit. The local temperatures in the flame have been determined previously by radiation-corrected Pt-Pt/Rh thermocouple measurements. Although a matter of convenience in this case, it has been demonstrated that absorption scans across two spectrally adjacent carbon monoxide rotational lines which originate in different vibrational levels can be used for temperature measurements. This technique was applied to measurements in the diffusion flame system and excellent agreement was found with the thermocouple measurements (Miller et al., 1991).

FIG. 6 shows the absorption through the P(7)E1 rotational level of the $\nu 4$ vibrational band of methane near 1262 cm$^{-1}$ in the premixed flame, 4 mm above the burner surface and at an equivalence ratio of 1.85. In this spectral region there are a number of other potential absorbers in the flame including acetylene (through the $\nu 4+\nu 5$ combination band) and water. Therefore exact wavelength calibration is essential in these measurements. This was accomplished by collecting reference spectra for N$_2$O, CH$_4$ and C$_2$H$_2$ under scanning conditions identical to those used in the flame studies. N$_2$O has a "fingerprint" spectral signature in this region which can be unambiguously assigned Guelachvili, G., and Rao, K.N. (1986). *Handbook of Infrared Standards*. (Academic Press, Orlando). With these spectra as a guide, it is possible to assign the dominant features in the flame spectra. In the spectral region studied here there are two methane features and a water absorption in between them. In FIG. 6, only the lower energy methane line and the onset of the water absorption are shown.

One of the selection criteria for monitoring species identified above was a high sensitivity of species concentration to equivalence ratio, $\phi$. In this regard it is instructive to compare the behavior of the carbon monoxide and methane to $\phi$ in the two flame systems: the overall equivalence ratio of the fuel/air mixture in the premixed flame and the local equivalence ratio in the diffusion flame study. For the latter, the local equivalence ratio is defined in terms of the mixture fraction as:

$$\phi = \frac{\xi}{\xi_s}\left(\frac{1-\xi_s}{1-\xi}\right) \qquad (4)$$

where $\xi_s$ is the stoichiometric mixture fraction (0.055 for methane) and the mixture fraction is calculated using the combining rule of Bilger, R.W., and Stårner, S.H. (1990). On reduced mechanisms for methane-air combustion in nonpremixed flames. *Combust. Flame* 80, 135.

The graphs in FIGS. 7a and 7b compare the relative dependence of carbon monoxide and methane concentrations on equivalence ratio in the two flames, premixed flame, FIG. 7a, or diffusion flame, FIG. 7b. In both systems studied, there is a substantial CO concentration remaining at $\phi \leq 1$. In contrast, the methane has been nearly completely destroyed at this low a stoichiometry. It is also noteworthy to compare the ratios of concentrations at $\phi=2$ to $\phi=1$. For methane in the diffusion flame study, this ratio is greater than 10. For carbon monoxide in the same combustion system, it is less than 3.

What is claimed is:

1. A method for monitoring combustion emissions in a combustion chamber comprising the steps of:
   emitting a laser beam from a tunable diode laser source;
   optically splitting said laser beam using optical splitting means;
   directing a first portion of said split beam into a reference detector means where said first portion of said split beam is converted to an electronic reference signal;

directing a second portion of said split beam through a first window into said combustion chamber;

further directing said second portion of said split beam through a second window, opposite to said first window, out of said combustion chamber and to a sample detector means where said second portion of said split beam is converted to an electronic sample signal;

directing said electronic reference signal and said electronic sample signal to a system control and electronics means;

analyzing said electronic reference signal and said electronic sample signal in said system control and electronics means; and directing an electronic feedback signal from said system control and electronics means to said tunable diode laser source.

2. The method of claim 1, which comprises the further steps of directing an electronic signal from said system control and electronics means to a combustion control means; and directing a further electronic signal from said combustion control means to control implementation means in said combustion chamber.

3. The method of claim 2, wherein said control implementation means are members of the group consisting of air input controllers, fuel input controllers, and secondary oxidizer input controllers.

4. The method of claim 1, which comprises the further step of chopping said laser beam using a mechanical chopping means after said laser beam emitting step.

5. The method of claim 1, which comprises the further step of modulating said laser beam using frequency modulating means after said laser beam emitting step.

6. The method of claim 1, which comprises the further steps of chopping said laser beam using a mechanical chopping means after said laser beam emitting step; and modulating said laser beam using frequency modulating means.

7. The method of claim 1, wherein said combustion emissions which are monitored by said method are species having a strong correlation to destruction and removal efficiency, said correlation being determined by a strong sensitivity to equivalence ratio, $$\frac{X_{\phi=2.0}}{X_{\phi=1.0}} \geq 10 \quad (1)$$

wherein X is the mole fraction and $\phi$ is the equivalence ratio, and a concentration of at least 1 ppm.

8. The method of claim 7, wherein said combustion emissions which are monitored by said method are members of the group consisting of saturated, unsaturated, and substituted hydrocarbons ranging from $C_1$ to $C_4$; free radicals; chlorine-containing molecules; and oxygen-containing molecules.

9. The method of claim 1, wherein said combustion emissions arise from the combustion of hazardous waste in a combustion chamber.

10. A method for monitoring combustion emissions in a combustion chamber comprising the steps of:

emitting a first laser beam from a tunable diode laser source, said laser beam having a wavelength which is in the absorption range for said emissions;

directing said first beam through a first window into said combustion chamber;

further directing said first beam through a second window, opposite to said first window, out of said combustion chamber and to a sample detector means where said beam is converted to a first electronic sample signal;

directing said first electronic sample signal to a system control and electronics means;

then, emitting a second laser beam from a tunable diode laser source, said laser beam having a wavelength which is in the non-absorption range for said emissions;

directing said second beam through a first window into said combustion chamber;

further directing said second beam through a second window, opposite to said first window, out of said combustion chamber and to a sample detector means where said beam is converted to a second electronic sample signal;

directing said second electronic sample signal to a system control and electronics means; and comparing and analyzing said first and second electronic sample signals in said system control and electronics means.

11. The method of claim 10, which comprises the further step of directing an electronic feedback signal from said system control and electronics means to said tunable diode laser source.

12. The method of claim 10, which comprises the further steps of directing an electronic signal from said system control and electronics means to a combustion control means; and directing a further electronic signal from said combustion control means to said combustion chamber.

13. The method of claim 11, which comprises the further step of chopping said laser beam using a mechanical chopping means after said laser beam emitting step.

14. The method of claim 10, which comprises the further step of modulating said laser beam using frequency modulating means after said laser beam emitting step.

15. The method of claim 10, which comprises the further steps of chopping said laser beam using a mechanical chopping means after said laser beam emitting step; and modulating said laser beam using frequency modulating means.

16. The method of claim 10, wherein said combustion emissions which are monitored by said method are species having a strong correlation to destruction and removal efficiency, said correlation being determined by a strong sensitivity to equivalence ratio, $$\frac{X_{\phi=2.0}}{X_{\phi=1.0}} \geq 10 \quad (1)$$

wherein X is the mole fraction $\phi$ and is the equivalence ratio, and a concentration of at least 1 ppm.

17. The method of claim 16, wherein said combustion emissions which are monitored by said method are members of the group consisting of saturated, unsaturated, and substituted hydrocarbons ranging from $C_1$ to $C_4$; free radicals; chlorine-containing molecules; and oxygen-containing molecules.

18. A method for controlling a chemical processing operation, said method using infrared absorption of light by at least one gas-phase component, said method comprising the steps of:

detecting light absorption levels of said gas-phase components using detecting means having a tunable diode laser as a light source;

computing concentrations of said gas-phase components based on said light absorption levels;

determining a controlling action to be taken using a control algorithm; and implementing said controlling action using control implementation means.

* * * * *